United States Patent [19]

Kamen

[11] 4,380,234
[45] Apr. 19, 1983

[54] INFUSION NEEDLE ATTACHMENT

[75] Inventor: Dean Kamen, Hooksett, N.H.

[73] Assignee: Baxter Travenol Laboratories, Inc., Deerfield, Ill.

[21] Appl. No.: 67,058

[22] Filed: Aug. 16, 1979

[51] Int. Cl.$^3$ .............................................. A61M 5/00
[52] U.S. Cl. ................................................... 604/180
[58] Field of Search ............... 128/214 R, 772, 218 N, 128/DIG. 26, 221

[56] References Cited

U.S. PATENT DOCUMENTS

| | | | |
|---|---|---|---|
| 3,064,648 | 11/1962 | Bujan | 128/214 R |
| 3,670,727 | 6/1972 | Reiterman | 128/214 R |
| 3,683,911 | 8/1972 | McCormick | 128/214 R |
| 4,129,128 | 12/1978 | McFarlane | 128/214 R X |
| 4,134,402 | 1/1979 | Mahurkar | 128/214 R |
| 4,170,993 | 10/1979 | Alvarez | 128/214 R |

Primary Examiner—Frank A. Spear, Jr.
Attorney, Agent, or Firm—Paul C. Flattery; John A. Caruso; Garrettson Ellis

[57] ABSTRACT

An infusion needle attachment which, although covering the infusion needle protruding from below, so as to effectively and desirably mask it from view at the injection site, is nevertheless also effectively used to guide the unseen needle into position, since a flap finger grip thereof is in the same plane as the needle and the user is thereby readily able to judge the desired location at which the point of the needle should make physical contact preparatory to the subcutaneous administration of a medicament to a patient using said needle.

4 Claims, 5 Drawing Figures

INFUSION NEEDLE ATTACHMENT

The present invention relates generally to infusion needle assemblies of the type using a needle-attached member for guiding and holding an infusion needle at its injection site, as exemplified by the needle assemblies of prior U.S. Pat. Nos. 3,064,648 and 3,856,020, and more particularly to improvements for the needle-attached member of such an assembly which does not inhibit the proper and accurate placement of the needle, and yet in use after such placement affords little or no visualization of the needle beneath the patient's skin, with significant beneficial pyschological effect on the patient. Said improvements are noteworthy in other respects, as will be described in greater detail subsequently.

It is already well known, as exemplified by prior U.S. Pat. No. 3,856,020, that an injection or infusion needle can be effectively guided into position by using as a finger grip a suitable member attached to the needle. The prior art needle-attached member typically has wings or lateral portions that are folded together and provide a convenient finger grip by which the needle is readily manipulated preparatory to being inserted into the patient. While generally effective, these prior art grips rely on visualization of the needle protruding therefrom to assist in the positioning thereof. Consequently, at the injection site there continues to be visualization of the needle beneath the patient's skin, which to some is psychologically upsetting, requiring the use of an appropriate bandage covering or the like.

Broadly, it is an object of the present invention to provide an improved infusion needle attachment overcoming the foregoing and other shortcomings of the prior art. Specifically, it is an object to provide a needle-attached member, by which an unseen needle, both during placement and thus also when in its injected position, is nevertheless accurately guided into said injected position.

As already noted, what is proposed herein is intended for use in combination with an infusion needle for achieving subcutaneous placement thereof incident to the dispensing therethrough of a medicament to a patient. Said improvement is an infusion needle attachment, and the embodiment thereof demonstrating objects and advantages of the present invention includes a disk-like body of a selected size adequate for delineating an operative area for making provision for the handling and for the positioning of the infusion needle. A hollow tubular member bounding a compartment for receiving said infusion needle is disposed in a peripheral location in said operative area and at an angular orientation in relation thereto so as to cause an infusion needle seated in said compartment to project at said angular orientation in depending relation from beneath the body. Further, in a medial location in said operative area there is provided an upstanding finger grip means foldably attached to the body along a line coincident with the center of the body and in aligned relation to the projecting infusion needle. As a result of the aligning orientations of the finger grip means and of the infusion needle, it has been found to be a relatively easy task to effectively guide the infusion needle into its required subcutaneous position even though the body is in covering relation thereover masking the presence of the needle during positioning. Said body also masks the needle after it has been positioned.

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein:

FIG. 2 is a perspective view illustrating an infusion needle with tubing in its assembled condition to the within improved attachment for same;

Figures 1, 2, 3, 4, 5:
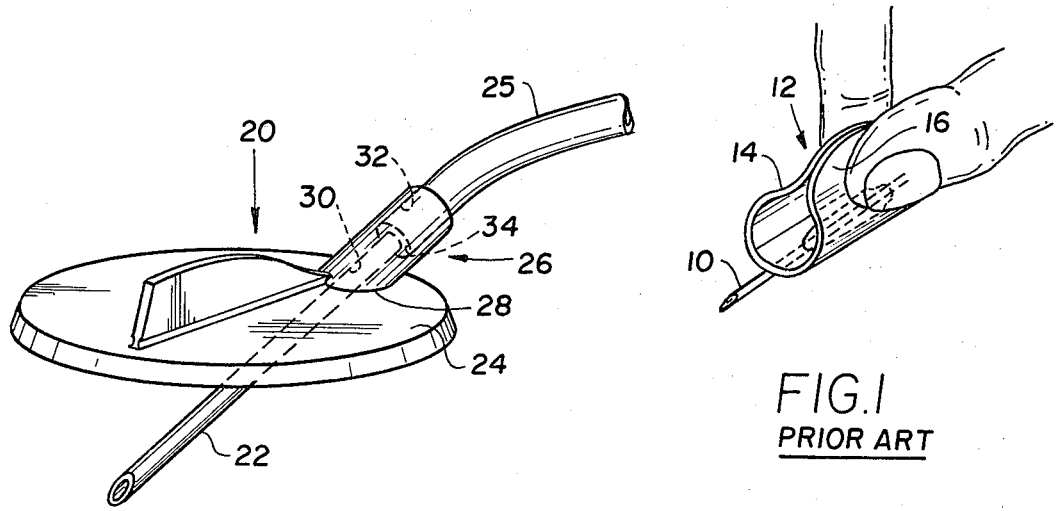
FIG. 1 is a perspective view of a prior art assembly of an infusion needle and a cooperating attachment thereto intended to facilitate the positioning of said needle.
FIGS. 2-5 illustrate the within improved attachment for facilitating the positioning and handling of an infusion needle. More particularly.

FIG. 3 is a side elevational view of the assembly illustrating further structural details; and FIGS. 4 and 5 are front elevational views illustrating the infusion needle and attachment in typical subcutaneous injected position within a patient, FIG. 4 illustrating the grip of the attachment in its initial upstanding condition, while FIG. 5 illustrates the said grip, as well as the attachment per se, in its subsequent condition adhesively secured to the patient.

It is already well known, as illustrated in FIG. 1 depicting the prior art, that it is advantageous in placing an infusion needle 10 in a selected injection site on a patient to use a needle-attached member 12 to more conveniently handle and guide the needle into place. Prior art member 12 is typically of elastomeric construction material so that, as illustrated in FIG. 1, lateral portions 14 and 16 thereof can be folded together and gripped between the fingers, as illustrated, to contribute to facilitated positioning of the needle. The assembly of needle 10 and attachment 12, as just generally described, is more particularly described and illustrated in prior U.S. Pat. No. 3,856,020, and is but one of many different types of needle-attached members which are provided to facilitate the handling and placement of infusion needles. Another prior patented assembly that is worth mentioning, because it is believed to have been the first, is that described and illustrated in prior U.S. Pat. No. 3,064,648.

Intended primarily as an improvement over the above referred to prior art needle-attached members, there is described and illustrated herein a member, also used in practice by being attached to an infusion needle, that is capable, in a unique manner, of assuring the correct angle and depth of penetration of the infusion needle in subcutaneous tissue. Equally important, and as will be described in detail subsequently, the within improved attachment for the infusion needle also effectively, at the injection site, masks the needle from view and this, in practice, has been found to provide a significant psychological advantage in obtaining the patient's compliance with requirements which enhance the use of the infusion needle for delivery of a medicament. That is, one of the significant advantages of the within attachment is that in use there is little or no visualization of the needle beneath the patient's skin, and this has proven to have a significant beneficial psychological effect on the patient.

To achieve the aforesaid and other benefits, there is provided according to the present invention a member, generally designated 20, intended in its contemplated use to be in attached relation to an infusion needle 22 which itself is attached in an appropriate manner to tubing 24 which, in a well understood manner, is connected to a reservoir, such as a syringe or pouch, containing a source of medicament or fluid for subcutaneous administration to a patient. Member 20, in a preferred embodiment, has a disk-like body 24 which delineates an operative area on the upper surface thereof, which area in terms of size and accessibility is both appropriate and adequate for components, as will now be described, which facilitate the referred to handling and placement of the infusion needle 22.

More particularly, one of the components is a tubular member 26 which, critical to the within invention, is advantageously located at the periphery of disk 24, as at 28, and is set at a selected angular orientation, which is typically approximately 30 degrees, as illustrated. The significance of the location 28 for the tubular member 28 is perhaps best appreciated by reference to FIG. 3. More particularly, said peripheral location 28 effectively locates the entire extent of disk 24 forward of the needle-receiving tube 26, and thus in an advantageous position to mask the presence of the needle 22 which projects in depending relation from beneath the disk 24. This is to be contrasted with what exists in the prior art as illustrated in FIG. 1 wherein the prior art needle 10 projects beyond the positioning member 12 and thus is visible at the injection site unless, of course, it is otherwise masked from view by a tape or bandage. In this connection, the presence of the injection end of needle 10 in the patient is due primarily to the assembly of needle 10 in a central location of attachement 12, a location undoubtedly believed necessary to use in order to enable the lateral portions or wings 14 and 16 to be gripped as in the manner illustrated in FIG. 1. It should be noted that it is not an acceptable solution to merely enlarge the size of member 12 so that it extends in covering relation over the prior art needle 10, since this will produce an unwieldy and difficult-to-handle size in the member 12.

As may perhaps best be appreciated from FIG. 2, the internal construction for the tubular member 26 will be understood to consist of a through bore 30 sized to accommodate the cylindrical infusion needle 22 and a larger-diameter counter bore 32 sized to accommodate a cylindrical tube 25. At the intersection of counter bore 32 with the through bore 30 there is of course presented a shoulder 34 which, in a well understood manner, during the injection of the assembly of needle and tube 22, 25 into the internal compartment 30, 32 formed within the tubular member 26 effectively serves as a stop or seat 34 for the larger diameter tube 25. Thus, shoulder 34 effectively limits the extent to which the infusion needle 22 per se projects beyond the undersurface of the disk 24. As a result, shoulder 34 thus effectively correspondingly limits the depth of penetration of the infusion needle during its placement in subcutaneous tissue 38.

Still referring to FIG. 3, it should also be readily appreciated that the angular orientation of tubular member 26 is correspondingly imparted to infusion needle 22, said angle, herein denoted by the reference numeral 36, being typically approximately 30 degrees.

Unlike the prior art attachment member used in the manner illustrated in FIG. 1, member 20 hereof does not require the folding together of lateral portions, an operational requirement which, in any event, would not be particularly desirable since it might modify the angle of entry 36 of the needle 22. Rather, and in accordance with the present invention, it is more desirable that the angle 36 be maintained between the needle 22 and the flat disk 24 so that the needle 22 is properly guided into its injection position at said angle 36. Thus, in accordance with the present invention, member 20 is provided with other gripping means. More particularly, said means, designated 40, consists of a flap 40 advantageously located, as is perhaps best illustrated in FIG. 4, along a line which is coincident with the diameter of the disk 24. Also as best illustrated in FIG. 4, flap 40 and needle 22 are in aligned relation, and this contributes to effective placement or guiding of the needle into an infusion site, even though needle 22 is essentially hidden below the disk 24. That is, the plane of flap 40 is the same as that of needle 22 and this the user is well cognizant of during placement of the needle, and is thereby readily able to judge the exact location at which the point of the needle 22 will make physical contact with the tissue 38.

After placement of the assembly 20 of the needle and its cooperating attachment 22, 24, an adhesive strip 42 is advantageously placed thereover, as in the manner illustrated in FIG. 5, to cause the folding of flap 40 flat against the disk 24, and the disk 24 to take on or conform in shape to the patient's anatomy at the injection site 38.

While the embodiment above described in connection with FIGS. 2–5 is preferred, there are of course modifications that can be made thereto, that are within the contemplation of the present invention. As an example, disk 24 may be constructed to contain a pocket which should be filled with a topical antiseptic which would come into direct contact with the user's skin, and/or the construction material of the disk and flap 24, 40 could be a suitable flexible plastic, rather than an elastomeric, and still allow the folded and shape-conforming condition depicted in FIG. 5. Also, to assist the adhesive strip 42 in holding disk 24 against the patient, the bottom surface of the disk 24 can advantageously be provided with an adhesive coat that is exposed, when needed during positioning, upon removal of a backing strip. In other respects as well, a latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. In combination with an infusion needle for achieving subcutaneous placement thereof incident to the dispensing therethrough of a medicament to a patient, an infusion needle attachment comprising a disk-like body of a selected size adequate for delineating an operative area for making provision for the handling and for the positioning of said infusion needle, a hollow tubular member bounding a compartment for receiving said infusion needle disposed in a peripheral location in said operative area and at an angular orientation in relation thereto so as to cause an infusion needle seated in said compartment to project at said angular orientation in depending relation from beneath said body, and an upstanding flap of a foldable construction material foldably attached to said body along a line coincident with the center of said body and in aligned relation to said projecting infusion needle, said flap being in a medial location of said operative area and extending in spanning relation from said tubular member to a point adjacent a peripheral edge of said body so as to effectively serve as a finger grip during said subcutaneous placement of said infusion needle, whereby said aligning orientations of said flap and infusion needle contributes to the proper guiding of said infusion needle into said required subcutaneous position thereof with said body in covering relation thereover masking the presence of said position needle.

2. The combination as claimed in claim 1, wherein the construction material of said body and of said flap is elastomeric, whereby said body is readily adapted to assume a curvature conforming to the curvature of the patient's anatomy receiving said infusion needle and said finger grip means is readily foldable flat against said body.

3. The combination as claimed in claim 1, wherein the construction material of said body and of said flap is flexible plastic, whereby said body is readily adapted to assume a curvature conforming to the curvature of the patient's anatomy receiving said infusion needle and said flap is readily foldable flat against said body.

4. The combination as claimed in claim 1, wherein said compartment of said tubular member is comprised by a through bore and a counter bore to thereby present a shoulder therealong, whereby said infusion needle is adapted to be attached to tubing and said tubing seats against said shoulder during the projection of said infusion needle through said through bore.

* * * * *